United States Patent [19]

Spielberg

[11] Patent Number: 5,501,666
[45] Date of Patent: Mar. 26, 1996

[54] NEEDLELESS INJECTOR

[75] Inventor: Jerry Spielberg, Willingboro, N.J.

[73] Assignee: Mycone Dental Supply Co., Cherry Hill, N.J.

[21] Appl. No.: 453,133

[22] Filed: May 24, 1995

[51] Int. Cl.$^6$ ..................................................... A61M 5/30
[52] U.S. Cl. ............................................. 604/68; 604/135
[58] Field of Search .................................. 604/68, 71, 72, 604/133, 134, 135, 232, 236, 237, 246, 247

[56] References Cited

U.S. PATENT DOCUMENTS

| 3,461,867 | 8/1969 | Zimmet et al. | 128/173 |
|---|---|---|---|
| 4,722,728 | 2/1988 | Dixon | 604/68 |
| 4,941,880 | 7/1990 | Burns | 604/68 X |
| 5,024,656 | 6/1991 | Gasaway et al. | 604/68 X |
| 5,049,125 | 9/1991 | Accaries et al. | 604/68 |

OTHER PUBLICATIONS

Mizzy, Inc., Syrijet Mark III brochure (circa 1968).
Mizzy, Inc., Syrijet Mark II brochure (circa 1968).
Mizzy, Inc., Syrijet Mark II product information sheet (circa 1968).
Mizzy, Inc., assembly drawings MJ–1841–B, MJ–1707–C, MJ–1700–G, and SA–6276 (Jan. 1988).
Greenfield, William and Karpinski, Joseph F., Needleless Jet Injection in Comprehensive Pain Control and Applications to Oral Surgery, Anethesia Progress, Jul.–Aug. 1972.
Bennett, C. Richard and Monheim, Leonard M., Production of Local Anesthesia by Jet Injection, Oral Surgery, Oral Medicine, Oral Pathology, vol. 32, No. 4, pp. 526–530, Oct. 1971.
Mott, M. G. and Stevenson, P. A., The Use of the Syrijet to Attain Local Anaethesia in Children with Acute Leukaemia, The British Journal of Clinical Practice, vol. 27, No. 11, Nov. 1973.
Hardison, Lt Col C. D., Application of a Versatile Instrument for Production of Cutaneous Anesthesia Without Needle Penetration of the Skin, JACEP, 1977.
Bennett, Richard C., et al., Studies on Tissue Penetration Characteristics produced by Jet Injection, JADA, vol. 83, Sep. 1971.
Mumford, David M. and Jackson, Pamela L., The Successful Use of Jet Anesthetic Injections with Childhood Lacerations, Clinical Pediatrics, vol. 15, No. 10, Oct. 1976.
Smith Karen A., et al., Jet Injection Anesthesia—a technique for painless bone marrow aspiration, The Journal of Pediatrics, vol. 85, No.5, pp. 731–732, Nov. 1974.
Denne, Jean R., et al., A Survey of Patient Preference for Insulin Jet Injectors Versus Needle and Syringe, The Diabetes Educator, vol. 18, No. 3, May/Jun. 1992.
Bioject Brochure re Biojector®2000, 1992.

Primary Examiner—John D. Yasko
Attorney, Agent, or Firm—Panitch Schwarze Jacobs & Nadel

[57] ABSTRACT

A needleless injector for providing medication provides improved flow rate with a reduced pressure head. The injector includes discharge member having a rounded or sloped jet orifice, a milled valve member, and a check valve, which provide for increased shot velocity, reduced time of the shot and increased flow.

15 Claims, 2 Drawing Sheets

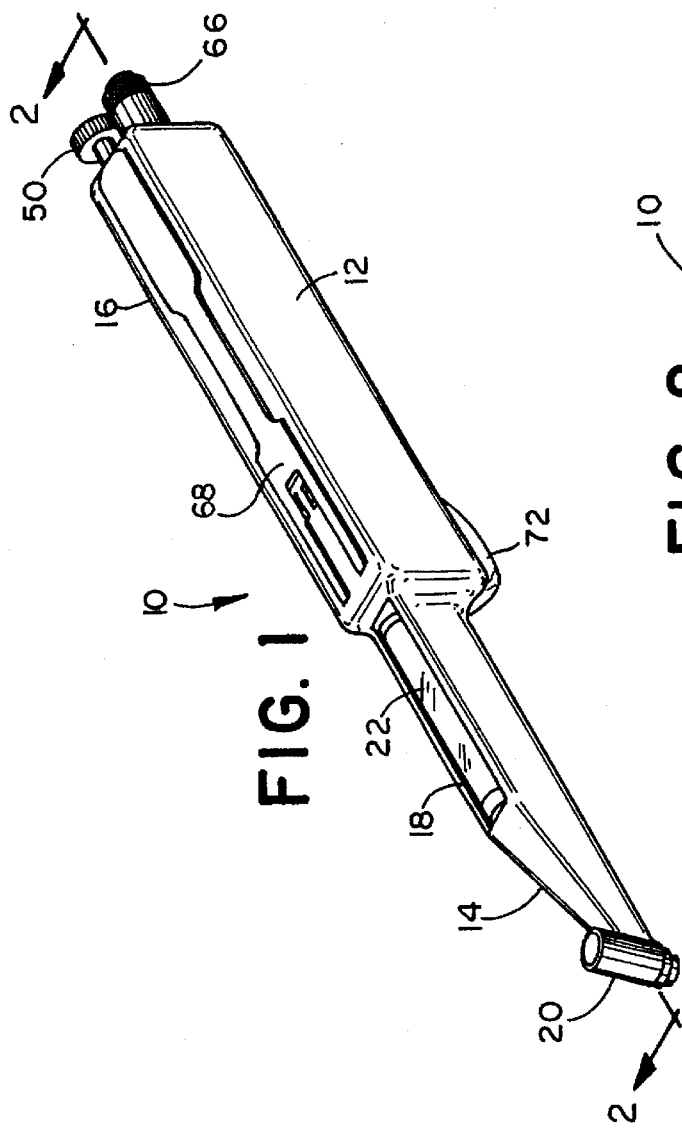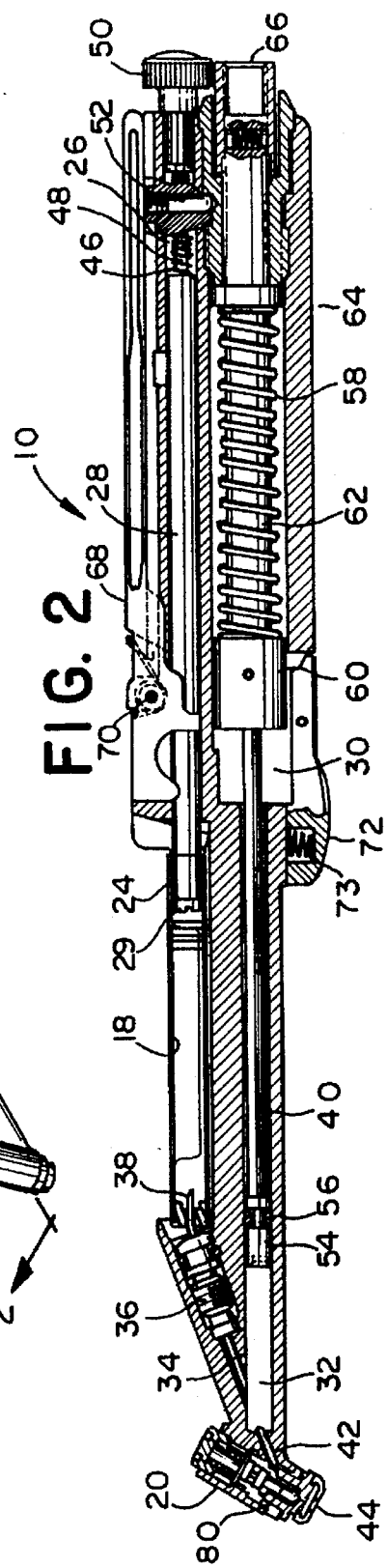

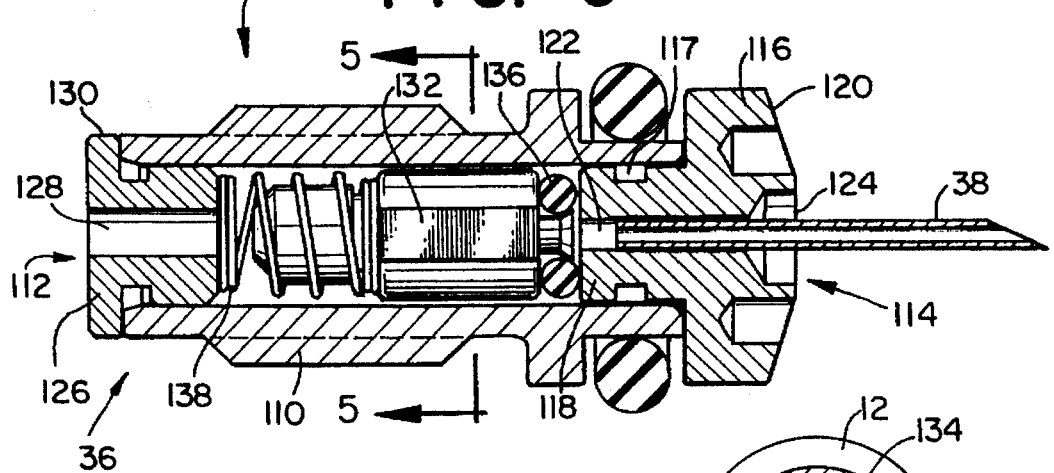
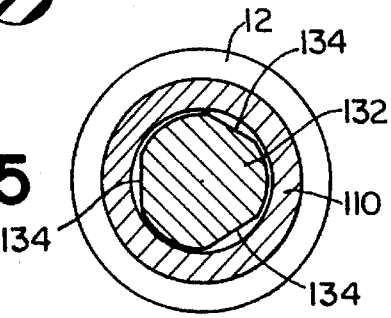
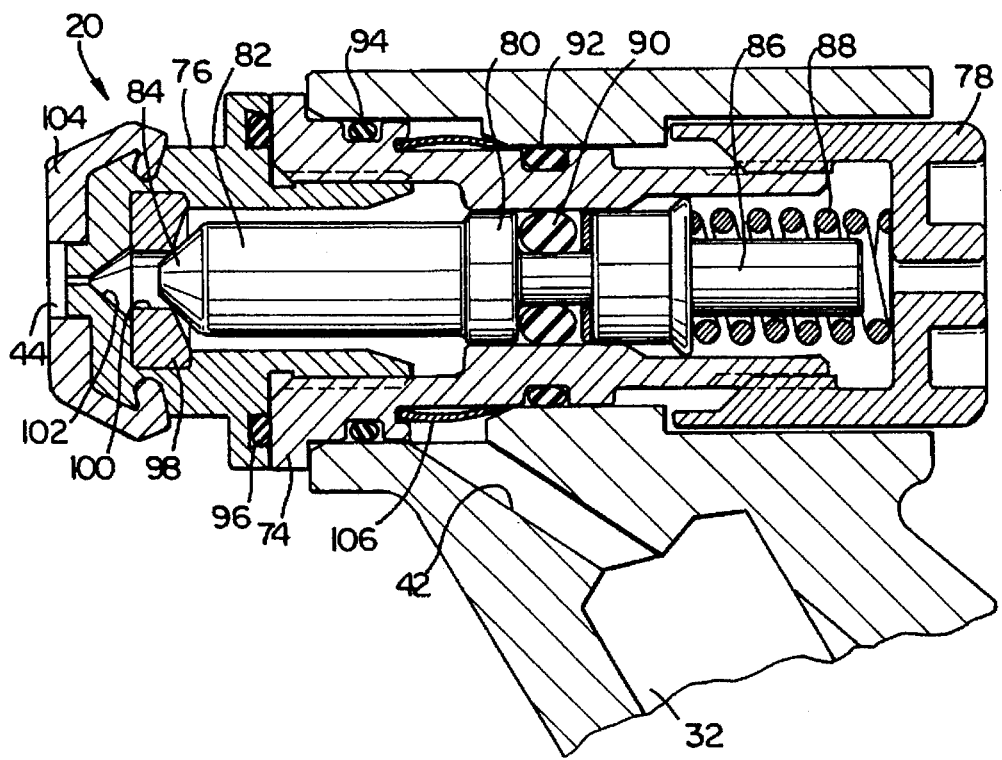

5,501,666

NEEDLELESS INJECTOR

FIELD OF THE INVENTION

The present invention relates to an injector, and more particularly, to a needleless injector having a jet orifice.

BACKGROUND OF THE INVENTION

Many types of medication are provided by syringes using needles which puncture a patient's skin or epidermis in order to inject the medication into the patient. Although commonly used, syringes have many drawbacks, such as deep structure injury due to the lacerating tip of the needle, possibilities of infection from contaminated needles, disposal problems and patients having a strong aversion to needles. Accordingly, there exists a need for alternative methods of delivering medication to patients.

Alternative methods of delivering medication have been developed. One known method is to deliver medication using a needleless injector. A needleless injector delivers medication by providing a strong, high pressure blast of the medication through a small orifice, which causes a minute stream of the medication to exit the orifice at a high rate of speed, thereby allowing the medication to penetrate into the skin and subcutaneous tissues. Although in use for many years, needleless injectors are not as prevalently used as syringes, due to, among other reasons, problems associated with the resistance of the skin which inhibits adequate delivery of medication.

The present invention is directed to an improved needleless injector having, inter alia, an improved discharge mechanism and orifice structure which provide a more even distribution and higher velocity jet which dispenses the selected volume in a shorter time period. A higher velocity jet allows the injector to be used for administering any drug intermuscularly. Additional benefits, such as reduced force required to dispense liquid and easier tension setting or cocking of the spring are also provided. The present invention also provides an improved design which is less susceptible to leakage, less costly to manufacture and easier to maintain than prior art needless injectors.

SUMMARY OF THE INVENTION

Briefly stated, the present invention is a piston actuated needleless injector comprising an elongated main body member having a first section and a second section. The first section includes a longitudinal cavity for receiving an ampule. The ampule has a first end and a second end and contains a liquid to be discharged from the injector. The main body member has a first longitudinal passageway extending between the cavity and the second section. A second longitudinal passageway extends between the first section and the second section and includes a discharge chamber. A conduit extends between the cavity and the discharge chamber.

A holder is provided for removably retaining the ampule within the cavity and a plunger located within the first passageway is shiftable into the cavity and into the ampule second end for pressurizing the liquid therein. A needle is provided for piercing the ampule first end and provides a means for the liquid to exit from the ampule to the discharge chamber by way of the conduit. A piston member axially movable within the second passageway pressurizes the liquid within the discharge chamber. The piston member defines a movable boundary for increasing and decreasing the volume of the discharge chamber. A discharge mechanism is located at a free end of the first section for discharging the liquid from the injector.

A check valve assembly is located in the conduit between the ampule and the discharge chamber and prevents backflow of liquid from the discharge chamber to the ampule. The check valve assembly comprises a hollow main body, a head piece, a retainer, a generally cylindrical valve member, an O-ring, and a spring. The hollow main body has a first end and a second end. The head piece has a narrow axial bore therein, a first section and a second section, the first section having a smaller cross-section than the second section and being secured within the second end of the check valve main body. The bore receives the needle and allows liquid to flow from the ampule into the check valve assembly. The retainer has an axial bore therein, a first section and a second section, the second section has a smaller cross-section than the first section and is secured within the first end of the check valve main body. The generally cylindrical valve member is disposed within the check valve main body between the head piece and the retainer for preventing liquid backflow. The O-ring is disposed within the check valve main body between the valve member and the head piece for providing a seal between the head piece and the valve member. The spring is disposed within the check valve main body between the valve member and the retainer for biasing the valve member against the O-ring.

Further, the discharge mechanism has a discharge passage with a jet orifice at an outer end thereof and a conical cavity upstream of the jet orifice. A pressure sensitive valve, with a conical shaped tip corresponding to the conical cavity, provides liquid communication between the jet orifice and the discharge chamber for discharging the liquid from the injector.

BRIEF DESCRIPTION OF THE DRAWING

The foregoing summary, as well as the following detailed description of the preferred embodiment of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings:

FIG. 1 is a perspective view of a needleless injector in accordance with the present invention;

FIG. 2 is a cross-sectional view of the needleless injector shown in FIG. 1, taken along lines 2—2 of FIG. 1;

FIG. 3 is an enlarged cross-sectional view of a check valve assembly of the needleless injector shown in FIG. 1;

FIG. 4 is an enlarged cross-sectional view of a discharge mechanism of the needleless injector shown in FIG. 1; and FIG. 5 is an enlarged cross-sectional view of a valve member of the needless injector shown in FIG. 3, taken along lines 5—5 of FIG. 3.

DETAILED DESCRIPTION OF PREFERRED EMBODIMENT

Certain terminology is used in the following description for convenience only and is not limiting. The words "right," "left," "lower" and "upper" designate directions in the drawing to which reference is made. The words "inwardly" and "outwardly" refer to directions toward and away from, respectively, the geometric center of the needleless injector and designated parts thereof. The terminology includes the words above specifically mentioned, derivatives thereof and words of similar import.

Referring now to the drawings in detail, wherein like numerals are used to indicate like elements throughout the several views, there is shown in FIG. 1 a needleless injector, generally designated 10, in accordance with the present invention. The needleless injector 10 is preferably used for injecting medication, such as anesthesia, into humans. While it is preferred that the needleless injector 10 be used for injecting anesthesia and medication into humans, it is understood by those skilled in the art from this disclosure that the needleless injector 10 could be used for other purposes, such as injecting other liquids, including solutions and suspensions, into humans or injecting liquids, including solutions and suspensions into animals, without departing from the spirit and scope of the invention.

The injector 10 is piston actuated in a manner similar to the needleless injector disclosed in U.S. Pat. No. 3,461,867, the disclosure of which is incorporated herein by reference. Although the present invention comprises a piston actuated type injector, it will be apparent to those of ordinary skill in the art from this disclosure that the features of the injector 10, as discussed in more detail below, can be applied to injectors actuated by other means, such as a compressed gas actuator type injector.

The injector 10 of the present invention comprises an elongated main body member 12 having a first section 14 and a second section 16 and is generally sized to fit within the palm of a user's hand. The injector 10 may be either circular or rectangular in cross-section, or a combination of circular and rectangular. In addition, the cross-sectional area of the first section 14 and the second section 16 may vary in size, as is shown in FIG. 1. In the presently preferred embodiment, the second section 16 is larger in cross-section than the first section 14. In the present embodiment, it is preferred that the main body member 12 be generally rectangular in cross section such that the main body member 12 is generally in the form of a parallelepiped. While it is preferred that the main body member 12 be generally in the form of a parallelepiped, it is understood by those skilled in the art from this disclosure that the main body member 12 could be shaped in other manners without departing from the spirit and scope of the invention. For instance, the main body member 12 could be generally in the form of a circle, oval, ellipse, triangle, or pentagon in cross section. Similarly, the first and second sections 14, 16 could be of similar dimensions and of similar size in cross-section.

The length of the injector 10 is such that the injector is comfortable to hold, and is generally from 12 to 16 inches in length. The injector 10 may be made of any strong and durable material which is capable of repeated use over a long period of time without degrading or wearing such that liquid within the injector 10 will not leak therefrom, and also is capable of being sterilized, such as by boiling, cold sterilizing, or with an autoclave. In the present embodiment, it is preferred that the injector 10 be constructed of generally rigid, high-strength, fluid impervious material, such as stainless steel. However, it will be apparent to those of ordinary skill in the art that the injector 10 may be constructed of other suitable materials, such as other metals, composites, plastic, or combinations of such materials.

The first section 14 of the injector 10 includes a longitudinal cavity or well 18 proximate the second section 16 and a discharge head or mechanism 20 (shown in greater detail in FIG. 4) at its distal end. The cavity 18 is sized for receiving an ampule or cartridge 22 containing a liquid to be discharged from the injector 10. The main body 12 includes a holder 24 or lip projecting from the second section 16 partially into the first section 14 for holding and removably retaining the ampule 22 within the cavity 18.

The ampule 22 is generally cylindrical and is sized to hold a predetermined volume or dosage of anesthesia or medication. In the presently preferred embodiment, the cavity 18 is sized and shaped to receive an ampule 22, such as a standard 1.8 cc dental anesthetic cartridge. The ampule 22 is placed into the cavity 18 by sliding a first end of the ampule 22 under the holder 24 and then laying a second, opposite end of the ampule 22 flat within the cavity 18. The second end of the ampule 22 comprises a fixed penetrable seal and the first end of the ampule 22 comprises a movable seal which can be shifted axially into the ampule 22 to pressurize the liquid therein.

Referring now to FIG. 2, a cross-section of the needleless injector 10 is shown. The main body member 12 of the injector 10 has a first longitudinal passageway 26 extending between the cavity 18 and the second section 16. A plunger 28 is located within the first passageway 26 and is shiftable into the cavity 18 and into the first end of the ampule 22 for pressurizing the liquid held within the ampule 22. A bayonet cap 29 is located at one end of the plunger 28 proximate the cavity 18, and contacts the ampule 22 first end when the plunger 28 is moved axially, thus moving the ampule 22 first end to pressurize the liquid within the ampule 22 such that the liquid will exit the ampule 22 second end.

The main body member 12 of the injector 10 also has a second longitudinal passageway 30 which extends between the first section 14 and the second section 16. The second passageway 30 comprises a first length having a first diameter located in the second section 16 of the main body 12 and a second length having a second diameter located in the first section 14 of the main body 12, the second length comprising a discharge chamber 32. In the presently preferred embodiment, the second diameter, i.e. the diameter of the discharge chamber 32, is smaller than the first diameter.

A conduit 34 extends between the cavity 18 and the discharge chamber 32 to allow fluid communication therebetween. A check valve assembly 36 is located at one end of the conduit 34 between the discharge chamber 32 and the cavity 18, proximate the cavity 18, to prevent the backflow of liquid from the discharge chamber 32 to the ampule 22. A needle 38 projects from the conduit 34 into the cavity 18 and is provided for piercing the first end of the ampule 22 to allow the liquid in the ampule 22 to exit from the ampule 22 into the discharge chamber 32 by way of the conduit 34.

The needle 38 used in the present invention is a stainless steel needle which is microwelded to the check valve assembly 36. Microwelding the needle 38 to the check valve assembly 36 is preferred because in the present invention it is important that the needle 38 remain hard, yet be bendable. Needles constructed of other materials and secured to the check valve assembly 38 by other means, such as brazing, has been found to anneal the needle, which prevents the needle from bending.

The plunger 28, which moves axially in the first passageway 26 to pressurize the liquid in the ampule 22, is actuated by a plunger spring 46 which is sleeved over a plunger guide rod 48. A plunger release knob 50 and a locking pin in the form of a stop nut retainer screw 52 are provided for cocking and holding the plunger spring 46 after an ampule 22 has been placed in the cavity 18 in order to place and maintain pressure on the movable end of the ampule 22 via the bayonet cap 29. The plunger release knob 50 is rotatable between a first position which maintains the bayonet cap 29 against the ampule 22, and a second position which releases the plunger spring 46 tension and allows for the ampule 22 to be either retained within the cavity 18 or removed from the cavity 18. When the knob 50 is in the first position, the stop nut retainer screw 52 maintains the plunger spring 46 under tension.

A piston member 40 is axially movable within the second passageway 30 for pressurizing the liquid within the discharge chamber 32. The piston member 40 defines a movable boundary for increasing and decreasing the volume of the discharge chamber 32. The piston member 40 includes a chevron seal 54 and an O-ring 56 for pressurizing the liquid within the discharge chamber 32 and preventing flow or leakage of liquid around the piston 40 and into the first length of the second passageway 30 in the second section 16 of the main body 12.

The piston member 40 extends from the chevron seal 54 in the discharge chamber 32 to a first shield 60 and a piston stroke rod 62 located in the first length of the second passageway 30. A piston spring 58 surrounds the stroke rod 62 and extends from the first shield 60 proximate the discharge chamber 32 to a second shield 64 proximate the distal end of the second passageway 30. Axial movement of the second shield 64 allows the movable boundary defining the volume of the discharge chamber 32 to be adjusted. Accordingly, a volume adjustment or control mechanism 66 which moves the second shield 64 is provided at the distal end of the second passageway 30 (i.e. at the free end of the second section 16 of the main body 12), to allow a user to vary the size of the discharge chamber 32, and thus the volume of liquid to be dispensed. In the presently preferred embodiment, the volume of the discharge chamber 32 ranges between 0.05 cc to 0.35 cc.

The piston spring 58 is cocked by movement of a handle or lever 68 located on an outer surface of the main body 12 and pivotable about a handle pin 70. Movement of the handle 68 away from the main body 12 moves the first shield 60 towards the second shield 64 and compresses the piston spring 58 therebetween. A trigger mechanism 72 maintains the first shield 60 in position so that the piston spring 58 is held in the compressed state. Movement of the trigger mechanism 72 releases the first shield 60 and allows the piston spring 58 to axially move the piston in the discharge chamber 32 toward the discharge mechanism 20 very rapidly. The trigger mechanism 72 may comprise a finger actuated button accessible on the outer surface of the main body 12 of the injector 10. The trigger mechanism 72 includes a trigger return mechanism 73 which in the preferred embodiment comprises a coil spring. Since other types of trigger mechanisms are known to those of ordinary skill in the art and further details of the trigger mechanism 72 are not required for a complete understanding of the present invention, the trigger mechanism 72 will not be discussed in greater detail.

Referring now to FIG. 4, the discharge mechanism 20 located at a free end of the first section 14 discharges the liquid from the injector 10. Accordingly, liquid flow in the injector 10 is from the ampule 22, through the needle 38 and check valve assembly 36 and into and through the conduit 34 to the discharge chamber 32. Liquid in the discharge chamber 32 is then pressurized by movement of the piston 40 into the discharge chamber 32, forcing the liquid from the discharge chamber 32 through a discharge passage 42 and into the discharge mechanism 20. The liquid exits the discharge mechanism 20 through a jet orifice 44 at an outer end of the discharge mechanism 20.

The discharge mechanism 20 comprises a generally cylindrical orifice body 74 having a cone tip 76 at one end and an orifice retainer cap 78 at an opposite end thereof. The discharge mechanism 20 is secured to the free end of the first section 14 of the main body 12 of the injector 10. A pressure sensitive valve member 80 is located within the orifice body 74 between the cone tip 76 and the retainer cap 78. The pressure sensitive valve member 80 comprises a cylindrical valve element 82 having a cone shaped tip 84 which is axially movable within the orifice body 74. The valve element is attached to an orifice piston 86 surrounded by an orifice spring 88, which biases the valve element 82. A first O-ring 90 seals the orifice body 74 between the valve element 82 and the orifice piston 86 to prevent liquid from leaking to the piston area of the orifice body 74 and out the orifice retainer cap 78. Second and third orifice body O-rings 92, 94 are provided on either side of the discharge passage 42 on the orifice body 74 to prevent liquid leakage from the discharge passage 42. Additionally, a removable cone tip O-ring 96 is provided for sealing between the orifice body 74 and the cone tip 76. A removable tip seat 98 having a narrow cylindrical passageway 100 is disposed between the cone tip 76 and the valve element conical tip 84. A replaceable rubber head 104 is removably installed over cone tip 76. The purpose of the rubber head 104 is to act as a cushion between the injector 10 and the tissue of the patient. The passageway 100 is dimensioned such that the passageway 100 has a diameter which only allows the valve element conical tip 84 to partially extend thereinto. A filter 106 is located in the discharge passage 42 for filtering the liquid prior to the liquid passing the pressure sensitive valve member 80 and entering the orifice 44. The filter 106 filters any sediments which have leached out of the liquid contained in the ampule 22. If the liquid contained in the ampule is in the form of a suspension, the filter 106 is chosen to have apertures sized to allow any desired suspended particles through the filter. If desired, the filter 106 can be an optional component.

The cone tip 76 includes a conical cavity 102 upstream of the jet orifice 44 which corresponds to the conical tip 84 of the pressure sensitive valve element 82, and a pressure sensitive valve 76 providing liquid communication between the jet orifice 44 and the discharge chamber 32. The arrangement and the layout of the conical tip 84 of the valve element 82, the passageway 100 in the tip seat, the conical cavity 102, and the jet orifice 44 are such that the coefficient of contraction and the coefficient of velocity are at or approaching unity. Although prior art needleless injectors incorporating a sharp edge type orifice provided adequate shot velocity for injecting certain liquids into particular locations or particularly soft tissue, the present invention provides an improved approach configuration on the upstream side of the orifice 44 to provide for, inter alia, greater shot velocity.

While it is preferred that the cavity 102 be conical in shape and that the valve element 82 include a conical tip 84 to correspond to the configuration of the cavity 102, it is understood by those skilled in the art from this disclosure that the inner cavity 102 could be of other configurations. For instance, the inner cavity 102 could be shaped generally in the form of a triangle or pentagon, without departing from the spirit and scope of the invention, so long as the inner cavity 102 and the valve element 82 tip 84 provide for a coefficient of contraction and a coefficient of discharge approaching unity.

When injecting medication through tissue by pressure as opposed to by needle, it is important to achieve a high velocity fluid flow having avena contracta at the point of contact with the tissue (the vena contracta is the point where the flow achieves its narrowest cross-section downstream of the plane of the orifice). By providing the coefficient of contraction and the coefficient of velocity at or approaching unity, the product of these coefficients yields a discharge coefficient close to unity, which eliminates the requirement for determining the precise location of the vena contracta. The coefficient of contraction ($C_c$) is the ratio of the area of the jet at the vena contracta to the area of the orifice. With liquids, it is the critical section where the actual velocity approaches the theoretical velocity. Numerical values of $C_c$ range from approximately 0.54 to unity depending on the nature of the orifice fluid. The coefficient of velocity ($C_v$) is the ratio of the actual mean velocity of the jet at the vena contracta to the theoretical velocity due to the whole head of the orifice. The value of $C_v$ varies from 0.95 to very near unity. The vena contracta is the critical section at which the actual velocity most nearly approaches the theoretical velocity corresponding to $(2\ gh)^{1/2}$. The coefficient of discharge ($C_D$) is the ratio of the actual discharge to the theoretical discharge for the entire orifice area. $C^D$ is also the product of the contraction and the velocity coefficients.

Flow is defined as: $Q=A*V$;
where A=area of orifice (ft$^2$)
V=velocity of flow (ft/sec)
Velocity of flow is: $V=(2\ gh)^{1/2}$;
where V=ft/sec;
g=gravity
h=height of fluid over orifice (ft)
Actual flow is: $Q_A=C_D A\ (2\ gh)^{1/2}$ or $C_c C_v A\ (2\ gh)^{1/2}$.

For a sharp edge orifice, $C_D=0.61$ and for a sloped orifice, $C_D=0.97$. Inserting values into the foregoing equations illustrates that a well rounded or sloped orifice, as in the present invention, provides for a greater shot velocity, a corresponding increase in flow rate, and a reduced time of shot, compared to a sharp edge type orifice. In the presently preferred embodiment, the jet orifice 44 is provided with an internal diameter of approximately 0.006 inch or with an internal diameter of approximately 0.009 inch. Again, using the foregoing equations, these internal diameters of the jet orifice 44 have been found to provide adequate flow rate for delivering certain types of medications to particular anatomical locations. For instance, an internal orifice diameter of 0.006 inch is preferred for administering anesthesia for dental procedures and an internal orifice diameter of 0.009 inch is preferred for administering anesthetics for other procedures, such as for providing topical, subcutaneous and intramuscular anesthesia.

Referring now to FIG. 3, the check valve assembly 36 located in the conduit 34 between the cavity 18 and the discharge chamber 32 prevents backflow of liquid from the discharge chamber 32 to the cavity 18 and back into the ampule 22. The check valve assembly 36 comprises a hollow main body 110 having a first end 112 proximate the discharge chamber 32 and a second end 114 proximate the cavity 18.

A head piece 116 is secured partially within the second end 114 of the check valve main body 110. The head piece 116 has a first section 118, a second section 120, and a narrow axial bore 122 therein for receiving the needle 38, which provides fluid communication between the ampule 22 and the check valve main body 110. The first section 118 has a smaller cross-section than the second section 120 and is secured within the second end 114 of the check valve main body 110. The bore 122 has a wide mouth 124 for receiving the needle 38 so that it is not exceedingly difficult to insert the needle 38 into the bore 122. A notch 117 in the outer surface of the first section 118 of the head piece 116 provides a sink for impurities to flow to during brazing of the head piece 116 to ensure that the head piece has a very smooth and clean edge so that liquid will not leak from the check valve assembly 36.

A retainer 126 having an axial bore 128 therein is partially disposed within first end 112 of the check valve main body 110. The retainer 126 has a rim 130 around an outer edge thereof which abuts an outer edge of the second end 114 of the check valve main body 110, with the remainder of the retainer 126 being secured within the first end 112 of the check valve main body 110. Thus, it can be seen that the head piece 116 and the retainer 126 plug each end of the check valve main body 110, and include axial bores 122, 128, respectively for allowing fluid to flow through the main body 110. The head piece 116 and the retainer 126 may be friction fit within the main body 110. Alternatively and/or additionally, the head piece 116 and the retainer 126 can be secured using a suitable adhesive. A suitable adhesive is an adhesive which does not break down due to autoclaving or cold sterilization, such as an epoxy resin.

Prior art check valve designs comprised a one piece design; that is, the main body and the head piece comprised a unitary structure. The present invention provides that the main body 110 is constructed separately from the head piece 116. Providing a two piece design makes the interior critical sealing surfaces accessible. It has been found that the prior art single piece construction of the main body 110 was difficult to manufacture without chatter marks on its surface. It was further difficult to control burr removal from the inner surface of the body, with the chatter marks and burrs being the source of recurring leakage problems. Accordingly, the two piece design of the check valve assembly 36 makes the critical sealing surfaces accessible so that the tolerances of the critical sealing surfaces can be more tightly controlled.

The check valve assembly 36 further includes a generally cylindrical valve member 132 disposed within the check valve main body 110 between the head piece 116 and the retainer 126 for preventing liquid backflow from the discharge chamber 32 to the cavity 18. In the presently preferred embodiment, the valve member 132 comprises a poppet having two or more longitudinal flat portions 134 (FIG. 5) on its outer surface. The flat portions 134 are generally equidistantly circumferentially spaced from each other. Also in the presently preferred embodiment, a diametral clearance between an outer diameter of the valve member 132 and an inside wall of the check valve main body 110 is sufficiently small such that the valve member 132 is maintained on center. By providing a sufficiently small diametral clearance to maintain the valve member 132 on center and equidistantly spacing the flat portions 134, a substantially even distribution of liquid flow around the valve member 132 is provided when the valve member 132 is moved to an open position, as discussed in greater detail below. A sufficiently small diametral clearance in the present invention comprises the range 0.0037 inch to 0.0053 inch.

An O-ring 136 is disposed within the check valve main body 110 between the valve member 132 and the head piece 116 for providing a seal between the head piece 116 and the valve member 132. A spring 138 is disposed within the check valve main body 110 between the valve member 132 and the retainer 126 for biasing the valve member 132 against the head piece 116 and the O-ring 136 such that the valve member 132 and the O-ring 136 prevent liquid from either entering or exiting the axial bore 122 in the head piece 116.

The valve member 132 is movable between a normally closed position (due to the biasing force of the spring 138), in which liquid may not travel between the main body 110 and the head piece 116 and an open position, in which liquid may flow between the axial bore 122 and the main body 110. In the closed position, the valve member 132 and the O-ring 136 block the axial bore 122 in the head piece 116 and prevent liquid flow. In the open position, the valve member 132 is moved away from the head piece and the axial bore 122. In the presently preferred embodiment, the O-ring 136 is secured around a portion of the valve member 132 such that when the valve member 132 is moved to the open position, the O-ring is also moved away from the head piece 116.

As previously discussed, the valve member 132 is normally in the closed position. The valve member 132 is moved from the closed position to the open position by liquid exiting the ampule 22 via the needle 38, due to the bayonet cap 29 moving the movable seal in the first end of the ampule 22.

In use, the plunger release knob 50 is rotated in a first direction, e.g. counter-clockwise, and the plunger 28 is moved outwardly from the main body 12 of the injector 10. An ampule 22 containing a liquid is loaded into the cavity 18, with the movable seal end of the ampule adjacent to the plunger 28. With the ampule 22 loaded in the cavity 18, the ampule 22 is pushed forward so that the needle 38 punctures the seal in the ampule 22, allowing the liquid to flow from the ampule 22 into the needle 38. The plunger rod 48 is then moved back towards the main body 12 until the locking pin 52 is positioned to maintain the plunger spring 46 under tension, at which time the plunger release knob 50 is rotated in a second, opposite direction to maintain the plunger in the passageway 26.

The handle 28 is then repeatedly moved from its position adjacent the main body 12 to a position away from the main body (approximately 60 degrees), and back, the handle 28 pivoting about the pin 70, in order to cock the injector 10. Movement of the handle 28 away from the body 12 cocks the piston spring 58. When the handle 28 is in the cocked position, i.e. away from the main body 12, the volume control mechanism 66 may be adjusted to specify the amount of liquid to be injected. Movement of the handle 28 back towards the main body 12 advances the bayonet cap 29 into the ampule 22, thereby moving the liquid in the ampule 22 into the needle 38 with force sufficient to open the valve member 132 in the check valve assembly 36, thereby allowing the liquid to flow into the discharge chamber 32. With the piston spring 58 cocked and the liquid now in the discharge chamber 32, the check valve member 132 returns to the closed position and prevents the liquid from returning to the ampule 22.

The injector head 20 is then positioned in the location at which the liquid is to be dispensed and the trigger mechanism 72 is squeezed. The trigger mechanism releases the piston 40 from the cocked position and drives the piston into the discharge chamber 32, thereby pressurizing the liquid therein. The liquid is then forced through the discharge passage 42 and the filter screen 106 with pressure sufficient to move the valve element 82 and allow the liquid to pass through the orifice 44 at a velocity sufficient to allow the liquid to penetrate the tissue of the patient.

It will be appreciated by those skilled in the art from this disclosure that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A piston actuated needleless injector comprising:

an elongated main body member having a first section and a second section, the first section including a longitudinal cavity for receiving an ampule, the ampule having a first end and a second end and containing a liquid to be discharged from the injector, the main body member having a first longitudinal passageway extending between the cavity and the second section, a second longitudinal passageway extending between the first section and the second section, the second passageway including a discharge chamber, and a conduit extending between the cavity and the discharge chamber;

a holder for removably retaining the ampule within the cavity;

a plunger located within the first passageway shiftable into the cavity and into the ampule second end for pressurizing the liquid therein;

a needle for piercing the ampule first end and providing a means for the liquid to exit from the ampule to the discharge chamber by way of the conduit;

a piston member axially movable within the second passageway for pressurizing the liquid within the discharge chamber, the piston member defining a movable boundary for increasing and decreasing the volume of the discharge chamber;

a discharge mechanism in fluid communication with the discharge chamber located at a free end of the first section for discharging the liquid from the injector; and a check valve assembly located in the conduit between the ampule and the discharge chamber, the check valve assembly preventing backflow of liquid from the discharge chamber to the ampule, wherein the check valve assembly comprises:

a hollow main body having a first end and a second end;

a head piece having a narrow axial bore therein, a first section and a second section, the first section having a smaller cross-section than the second section, the first section being secured within the second end of the check valve main body, the bore receiving the needle and allowing liquid to flow from the ampule into the check valve assembly;

a retainer having an axial bore therein and a rim along an outer edge, the retainer being secured within the first end of the check valve main body such that the rim abuts an outer edge of the check valve main body;

a generally cylindrical valve member disposed within the check valve main body between the head piece and the retainer for preventing liquid backflow;

an O-ring disposed within the check valve main body between the valve member and the head piece for providing a seal between the head piece and the valve member; and a spring disposed within the check valve main body between the valve member and the retainer for biasing the valve member against the O-ring.

2. The needleless injector as recited in claim 1 wherein the valve member of the check valve assembly comprises a poppet, the poppet having at least two longitudinal flat portions on an outer diameter thereof, the flat portions being generally equidistantly circumferentially spaced from each other.

3. The needleless injector as recited in claim 1 wherein a diametral clearance between an outer diameter of the valve member and an inside wall of the check valve main body is sufficiently small such that the valve member is maintained on center thereby providing a substantially even distribution of liquid flow around the valve member when the valve member is moved to an open position.

4. The needleless injector as recited in claim 3 wherein the valve member comprises a poppet, the poppet having two or more longitudinal flat portions on an outer diameter thereof, the flat portions being equidistantly circumferentially spaced from each other.

5. The needleless injector as recited in claim 1 wherein the discharge mechanism includes a discharge passage with a jet orifice at an outer end thereof, a conical cavity upstream of the jet orifice, and a pressure sensitive valve providing liquid communication between the jet orifice and the discharge chamber, the pressure sensitive valve having a conical shaped tip corresponding to the conical cavity.

6. The needleless injector as recited in claim 5 wherein the discharge mechanism has a coefficient of contraction and a coefficient of velocity each approaching unity.

7. The needleless injector as recited in claim 5 further comprising a filter located between the discharge chamber and the discharge passage.

8. A piston actuated needleless injector comprising:

an elongated main body member having a first section and a second section, the first section including a longitudinal cavity for receiving an ampule, the ampule having a first end and a second end and containing a liquid to be discharged from the injector, the main body member having a first longitudinal passageway extending between the cavity and the second section, a second longitudinal passageway extending between the first section and the second section, the second passageway including a discharge chamber, and a conduit extending between the cavity and the discharge chamber;

a holder for removably retaining the ampule within the cavity;

a plunger located within the first passageway shiftable into the cavity and into the ampule second end for pressurizing the liquid therein;

a needle for piercing the ampule first end and providing a means for the liquid to exit from the ampule to the discharge chamber by way of the conduit;

a check valve assembly located in the conduit between the ampule and the discharge chamber, the check valve assembly preventing backflow of liquid from the discharge chamber to the ampule;

a piston member axially movable within the second passageway for pressurizing the liquid within the discharge chamber, the piston member defining a movable boundary for increasing and decreasing the volume of the discharge chamber; and a discharge mechanism in fluid communication with the discharge chamber located at a free end of the first section, the discharge mechanism having a discharge passage with a jet orifice at an outer end thereof and a conical cavity upstream of the jet orifice, and a pressure sensitive valve providing liquid communication between the jet orifice and the discharge chamber for discharging the liquid from the injector, the pressure sensitive valve having a conical shaped tip corresponding to the conical cavity.

9. The needleless injector as recited in claim 8 wherein the check valve assembly comprises:

a hollow main body having a first end and a second end;

a head piece having a narrow axial bore therein, a first section and a second section, the first section having a smaller cross-section than the second section, the first section being secured within the second end of the check valve main body, the bore receiving the needle and allowing liquid to flow from the ampule into the check valve assembly;

a retainer having an axial bore therein and a rim along an outer edge, the retainer being secured within the first end of the check valve main body such that the rim abuts an outer edge of the check valve main body;

a generally cylindrical valve member disposed within the check valve main body between the head piece and the retainer for preventing liquid backflow;

an O-ring disposed within the check valve main body between the valve member and the head piece for providing a seal between the head piece and the valve member; and a spring disposed within the check valve main body between the valve member and the retainer for normally biasing the valve member against the O-ring.

10. The needleless injector as recited in claim 9 wherein an internal diameter of the jet orifice is approximately 0.006 inch.

11. The needleless injector as recited in claim 9 wherein an internal diameter of the jet orifice is approximately 0.009 inch.

12. A needleless injector comprising:

an elongated main body member having a first section and a second section, the first section including a longitudinal cavity for receiving an ampule, the ampule having a first end and a second end and containing a liquid to be discharged from the injector, the main body member having a first longitudinal passageway extending between the cavity and the second section, a second longitudinal passageway extending between the first section and the second section, the second passageway including a discharge chamber, and a conduit extending between the cavity and the discharge chamber;

a holder for removably retaining the ampule within the cavity;

a plunger located within the first passageway shiftable into the cavity and into the ampule second end for pressurizing the liquid therein;

a needle for piercing the ampule first end and providing a means for the liquid to exit from the ampule to the discharge chamber by way of the conduit;

a piston member axially movable within the second passageway for pressurizing the liquid within the discharge chamber, the piston member defining a movable boundary for increasing and decreasing the volume of the discharge chamber;

a discharge mechanism in fluid communication with the discharge chamber for discharging the liquid from the injector located at a free end of the first section, the discharge mechanism having a discharge passage with a jet orifice at an outer end thereof and a conical cavity upstream of the jet orifice, and a pressure sensitive valve for providing liquid communication between the jet orifice and the discharge chamber, the pressure sensitive valve having a conical shaped tip corresponding to the conical cavity; and a check valve assembly located in the conduit between the ampule and the discharge chamber, the check valve assembly preventing backflow of liquid from the discharge chamber to the ampule, wherein the check valve assembly comprises:

a hollow main body having a first end and a second end;

a head piece having a narrow axial bore therein, a first section and a second section, the first section having a smaller cross-section than the second section, the first section being secured within the second end of the check valve main body, the bore receiving the needle and allowing liquid to flow from the ampule into the check valve assembly;

a retainer having an axial bore therein and a rim along an outer edge, the retainer being secured within the first end of the check valve main body such that the rim abuts an outer edge of the check valve main body;

a generally cylindrical valve member disposed within the check valve main body between the head piece and the retainer for preventing liquid backflow;

an O-ring disposed within the check valve main body between the valve member and the head piece for providing a seal between the head piece and the valve member; and a spring disposed within the check valve main body between the valve member and the retainer for biasing the valve member against the O-ring.

13. The needleless injector as recited in claim 12 wherein the valve member comprises a poppet, the poppet having two or more longitudinal flat portions on an outer diameter thereof, the flat portions being equidistantly circumferentially spaced from each other.

14. The needleless injector as recited in claim 13 wherein a diametral clearance between an outer diameter of the poppet and an inside wall of the check valve main body is sufficiently small such that the poppet is maintained on center thereby providing an even distribution of liquid flow around the poppet when the popper is moved.

15. The needleless injector as recited in claim 14 wherein the discharge mechanism has a coefficient of contraction and a coefficient of velocity each approaching unity.

* * * * *